(12) United States Patent
Yasuda et al.

(10) Patent No.: US 7,846,717 B2
(45) Date of Patent: Dec. 7, 2010

(54) CELL-CULTIVATION MICROCHAMBER

(75) Inventors: Kenji Yasuda, Tokyo (JP); Takanori Ichiki, Tokyo (JP); Kazunori Okano, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 1525 days.

(21) Appl. No.: 10/525,756

(22) PCT Filed: Aug. 26, 2003

(86) PCT No.: PCT/JP03/10758

§ 371 (c)(1),
(2), (4) Date: Aug. 2, 2005

(87) PCT Pub. No.: WO2004/018616

PCT Pub. Date: Mar. 4, 2004

(65) Prior Publication Data

US 2006/0014273 A1    Jan. 19, 2006

(30) Foreign Application Priority Data

Aug. 26, 2002    (JP) .............................. 2002-245904

(51) Int. Cl.
*C12M 1/00* (2006.01)
*C12M 3/00* (2006.01)
*C12M 1/34* (2006.01)

(52) U.S. Cl. .............. 435/292.1; 435/287.7; 435/287.8; 435/288.5; 435/305.2

(58) Field of Classification Search .............. 435/292.1, 435/287.7, 287.8, 288.5, 305.2; 219/121.85
See application file for complete search history.

(56) References Cited

U.S. PATENT DOCUMENTS

2003/0152756 A1 *    8/2003    Yamada et al. .............. 428/210

FOREIGN PATENT DOCUMENTS

| JP | 8-172956 | 7/1996 |
| JP | 10-191961 | 7/1998 |
| JP | 2001-17155 | 1/2001 |
| WO | 02/42411 | 5/2002 |

OTHER PUBLICATIONS

Moriguchi, H.; "An agar-microchamber cell-cultivation system: flexible change of microchamber shapes during cultivation by photo-thermal etching", May 2002, Lab Chip, 2, 125-130.*

* cited by examiner

*Primary Examiner*—William H Beisner
*Assistant Examiner*—Danielle Henkel
(74) *Attorney, Agent, or Firm*—Wenderoth, Lind & Ponack, L.L.P.

(57) ABSTRACT

A microchamber including a glass substrate which is transparent to a specific wavelength, an absorbent region which absorbs the specific wavelength, and a melting substance region which does not absorb the specific wavelength, is solid at room temperature and melts when heated, which regions are layered on the glass substrate. The absorbent region, is irradiated with a focused light beam of the specific wavelength and locally heated in the vicinity of the converging rays, so that the melting substance region is locally melted at a portion adjacent to the absorbent region, thereby forming a cavity as the focused light beam moves. Accordingly, the shape of the microchamber can be arbitrarily changed in accordance with the process of cell culture.

22 Claims, 11 Drawing Sheets

CELL-CULTIVATION MICROCHAMBER

TECHNICAL FIELD

The invention of the present application relates to a novel microchamber for cell culture capable of culturing cells one by one while observing the state of the cells under a microscope.

BACKGROUND ART

A change in the state of cells or response of cells to a chemical or the like has conventionally been observed as if the average of a cell group represented the property of one cell. In an actual cell group, cells which are synchronized in a cell cycle are not so many and cells express a protein at cycles different from each other. A method of synchronized culture has been developed with a view to overcoming these problems. Since the cells cultured are not cells derived from exactly the same cells, however, there is a possibility of causing a difference in the protein expression due to a difference in genes among the derived cells before cultivation. Upon actual analysis of a response to stimulation, it is very difficult to find whether fluctuations appearing in the results are attributable to the fluctuations in response which are common in the reaction mechanism of the cell itself or to a difference among cells (that is, a difference in genetic information). Since a cell line is usually not obtained by cultivating one cell, it is also very difficult to find whether or not the fluctuations in the reproduction of a response to stimulation are attributable to a genetic difference among cells. Stimulation (signal) to cells can be classified into two groups, that given by the amounts of a signal substance, nutrition and dissolved gas contained in a solution surrounding the cells therewith; and that given by a physical contact with another cell, which also makes the judgment on the fluctuations difficult.

When cell observation is carried out in the biotechnological research field, it is common practice to temporarily take out a portion of a cell group cultured using a large-sized incubator and observe the cells set on a microscope, or to control the temperature of the microscope while surrounding the entire microscope with a plastic container and carry out microscopic observation at a carbon dioxide concentration and humidity controlled using another small container inserted in the plastic container. Upon this observation, the conditions of a culture solution are kept constant by replacing a wasted culture solution with a fresh one, while culturing cells. According to the method as disclosed in Japanese Patent Laid-Open No. 10-191961, for example, the nutrition condition is kept constant by a mechanism in which a circulation pump moves the level of a medium relative to the surface of a base material up and down between a level higher than the upper end height of the base material and a level lower than its bottom end height, whereby a new medium is fed when the level is below the above-described low level and the medium is discharged when the level exceeds the high level. Disclosed in Japanese Patent Laid-Open No. 08-172956 is a culture apparatus, in which one end of each of an inlet pipe for introducing a new culture medium into a culture vessel, an outlet pipe for discharging the culture medium in the culture vessel to the outside, and a gas pipe permitting a gaseous portion in the culture vessel and a pump to communicate with each other is inserted in the culture vessel and filters for preventing the invasion of bacteria into the culture vessel are installed to the inlet pipe, outlet pipe and gas pipe, respectively. Thus, the nutrition conditions in a culture tank can be kept constant. In either one of these inventions, however, an example of culturing cells while controlling their solution environment and physical contact between cells is not known.

With a view to overcoming these problems, the inventors of this application invented a technology of selecting only one specific cell and cultivating it as a cell line, a technology of controlling the conditions of a solution environment of cells and keeping the cell density in the vessel constant upon cell observation, and a technology of cultivating and observing cells, which interact with each other, while specifying them and applying for patent on them as Japanese Patent Application No. 2000-356827.

The microchamber newly proposed by the present inventors has novel characteristics in its constitution. The microchamber is formed utilizing a microfabrication technology of glass or the like. Prior to the initiation of cultivation, the microchamber is formed on the glass surface and cell culture can be carried out by making use of its shape. It is therefore difficult to change, depending on the state after cultivation, the pattern of a flow path between the microchambers which path determines interaction between the microchambers. It is also difficult to change the shape of the microchamber itself in accordance with the progress of the cultivation.

In addition, a technology of heating the microchamber to change its shape by making use of a focused beam or the like cannot be applied to the heating in a three-dimensional local region smaller than the wavelength of infrared light.

An object of the present invention is therefore to provide a novel microchamber whose shape can be changed depending on the cultivation stage, based on the detailed investigation on the above-described microchamber developed by the present inventors. Another object of the present invention is to provide a novel microchamber for cell culture which permits spot heating of a nanoscale fine region.

SUMMARY OF THE INVENTION

The invention of the present application provides, in order to overcome the above-described problems, a microchamber for cell culture which comprises a substrate transparent to light of a specific wavelength, and a region which absorbs light of the specific wavelength and another region made of a solid which does not absorb light of the specific wavelength and has a melting point lower than the boiling point of water, for example, a substance which is a solid at normal temperature but is melted by heating, both regions being laid over the substrate. Further, the invention provides a cell culture apparatus with a unit of irradiating light having a specific wavelength, along with the microchamber.

More specifically, the cell culture apparatus according to the present invention has a unit of irradiating a focused beam having the specific wavelength to a specific region of the above-described microchamber for cell culture. The region of a solid substance which does not absorb light of the specific wavelength locally emits heat in the absorption region when exposed to a focused beam having the specific wavelength and by the resulting heat, the region of the solid substance existing adjacent to the absorption region is partially molten and dispersed. With the movement of a focused beam, it forms a space.

Also provided is a spot heating unit of a nanoscale fine region. It can carry out microscopic level drawing to form a nanoscale fine pattern of the absorption region, and expose the pattern to a focused beam, thereby spot-heating a region limited to a size as fine as the line width of a thin film layer and finer than the wavelength of the exposed light.

The microchamber for cell culture further comprises a semipermeable membrane which covers therewith the upper surface of the microchamber so as to block the cells from coming out of the chamber, has a pore size small enough to disturb the passage of cells through the film, and is optically transparent to the focused beam, and a unit permitting the replacement of a solution in the solution replacement section, in which a culture solution is circulated, on the upper surface of the semipermeable membrane.

BRIEF DESCRIPTION OF THE DRAWINGS

FIG. 11 is a schematic view illustrating a still further example of the constitution of the microchamber for cell culture.

DETAILED DESCRIPTION OF THE INVENTION

The invention of the present application has characteristics as described above. The embodiment of the invention will next be described.

Figure 1:
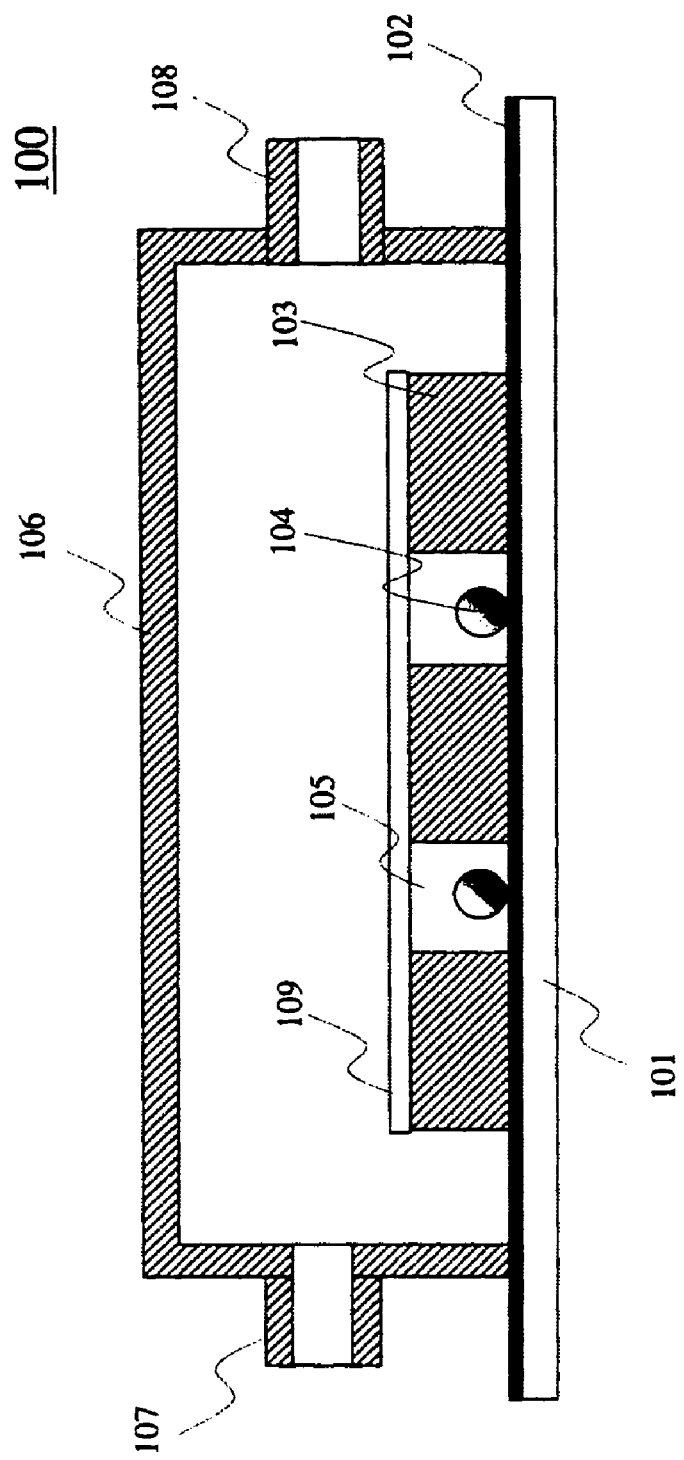
FIG. 1 is a schematic view illustrating one example of the fundamental constitution of the invention of the present application.

First, one example of the fundamental constitution of the microchamber for cell culture according to the invention of the present application will be described based on the example illustrated in FIG. 1. For example, as illustrated in FIG. 1, the microchamber 100 for cell culture according to the invention of the present application has an optically transparent substrate 101 such as slide glass and a thin film layer 102 laid thereover as an absorption layer exhibiting optical absorption such as a chromium deposited layer. Upon observation through a transmitted light, the thin film layer 102 is preferably thick enough not to absorb light completely and at the same time is thin without irregularities in thickness. When the absorption layer is made of chromium, it has a thickness of 50 Å and transmits about 70% of light in the visible range. Over the light absorption thin film layer 102, a region 103 of a substance such as agarose is laid which is optically transparent, has a low melting point and has no toxicity to cells such as. The substance of this region 103 is a solid substance, as defined by the invention of the present application, which does not absorb light of a specific wavelength and at the same time, having a melting point lower than the boiling point of water. Agarose is a typical example of it. The solid substance having a melting point not greater than 45° C. is usually preferred. In particular, agarose is harmless to cells, has less influence on the culture test data and is therefore the most appropriate substance, because it does not exhibit adhesion to cells and is not a signal substance for cells. In the region 103, a plurality of cavities 105 for introducing a sample such as cell 104 are formed in a mold upon formation of the region 103. In each cavity 105, a specific cell 104 is cultivated. The surface of the light absorption thin film layer 102 such as a chromium deposited layer may be subjected to silane formation treatment, followed by application and fixing thereto a cell absorptive factor such as collagen to permit stable adhesion of the cell 104 to the bottom surface of the cavity 105. As in this example, by covering the upper surface of the region 103 with an optically transparent semipermeable membrane 109 such as cellulose, contamination from outside world such as that by microorganisms can be prevented and at the same time, escape of the cell from the cavity 105 can also be prevented. When the region 103 is made of agarose and the semipermeable membrane 109 is cellulose, a portion of each of their saccharide chains is ring-opened, the —CHO residues are modified with avidin and biotin having an amino terminal, respectively, and the semipermeable membrane 109 is connected with the region 103 via the resulting avidin-biotin linkage. When circulation of a culture solution is necessary upon cultivation of the cell 104, an optically transparent container 106 large enough to cover the entire region 103 is laid over. The culture solution may be introduced from a tube 107, while the waste is collected from the tube 108.

Figure 2:
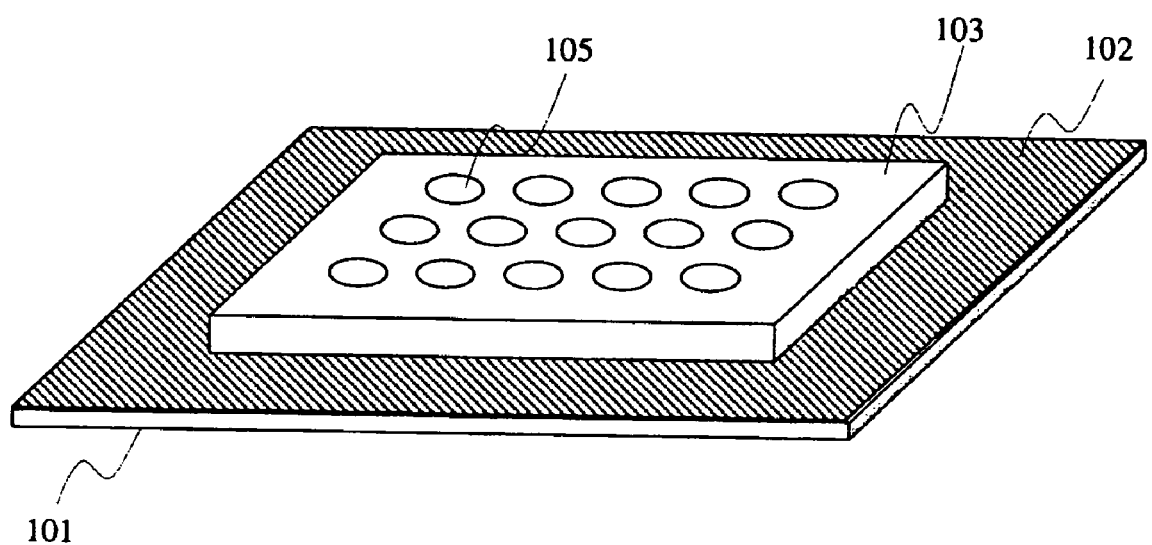
FIG. 2 is a schematic view illustrating the constitution of the microchamber for cell culture as illustrated in FIG. 1.

FIG. 2 illustrates one example of the arrangement of the cavities 105 formed in the region of a substance, such as agarose, which is optically transparent, has a low melting point and has no toxicity to cells and the like. As is apparent from this diagram, a plurality of cavities 105 are arranged in the region 103 and cells can be cultivated in these cavities after introduced therein.

Figure 3:
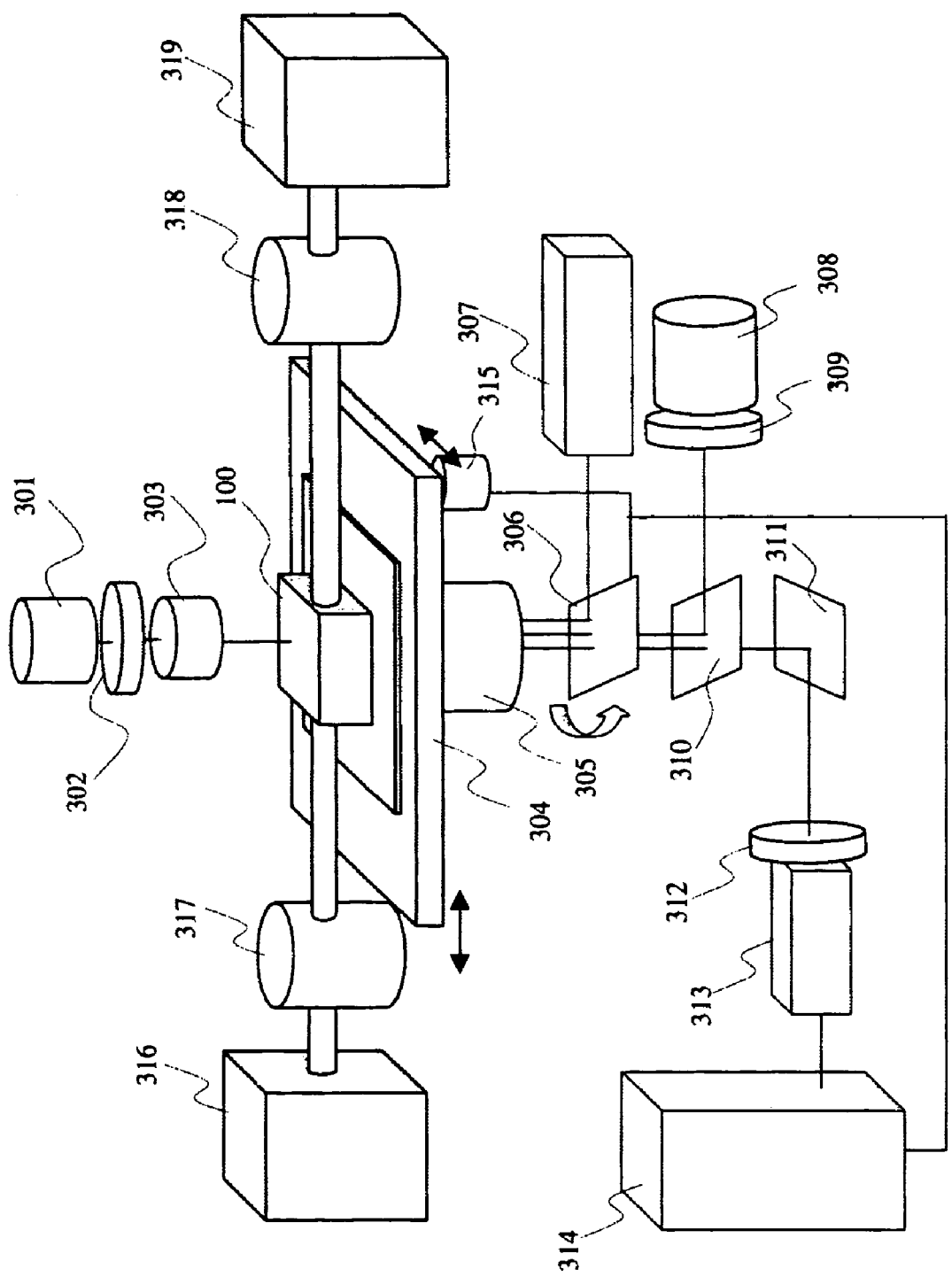
FIG. 3 is a schematic view illustrating one example of the constitution of an apparatus for observing the microchamber for cell culture as illustrated in FIG. 1 and spot heating using a focused beam.

FIG. 3 illustrates one example of the constitution of an apparatus for introducing a focused beam to change the shape of the region 103 of the microchamber 100 for cell culture. This apparatus is equipped with a microscopic observation system for observing a change in the state of a sample such as cell while cultivating it in the microchamber 100 for cell culture, a culture solution circulating system, and a focused beam irradiation system for changing the shape of the microchamber 100 for cell culture during cultivation. As is apparent from FIG. 3, the microchamber 100 for cell culture is placed on a light path of the microscopic observation system and culture solution feeding and discharging sections are connected to this microchamber 100 for cell culture. First, the constitution of the microscopic observation system will be described. Light irradiated from a light source 301 is adjusted to a specific wavelength by a filter 302, collected by a condenser lens 303, and irradiated to the microchamber 100 for cell culture. The light thus irradiated is used in the observation through an objective lens 305 as a transmitted light. The transmitted optical image inside of the microchamber 100 for cell culture passes through the filter 312 by a mirror 311, induced by a camera 313, and then focused onto the acceptance surface of the camera. The chamber 100 for cell culture is desirably made of an optically transparent material to light of a wavelength selected by the filter 302. Specific examples include glasses such as borosilicate glass and quartz glass, resins or plastics such as polystyrene, solid substrates such as silicon substrate and high molecular substances such as agarose. When a silicon substrate is employed, use of light having a wavelength of 900 nm or greater is taken into consideration. As described above in relation to the light absorption layer 102, selective use of a film thick enough not to permit 100% light absorption or selective use of a wavelength where no absorption is detected is desired.

The light irradiated from a light source 308 is introduced to an objective lens 305 by a dichroic mirror 310 after selection of the wavelength by a filter 309, and is used as an excitation light for fluorescent observation inside of the microchamber 100 for cell culture. The fluorescence emitted from the microchamber 100 for cell culture is collected by the objective lens 305 again. Only the fluorescence and transmitted light remaining after removal of the excitation light by the filter 312 can be observed by a camera 313. Only the transmitted light, only the fluorescence or both of the transmitted light image and fluorescence image can be observed by the camera 313 by changing the combination of the filters 302, 309 and 312.

The optical path has, inside thereof, a mechanism for introducing a laser light generated by a laser light source 307 into the objective lens 305 by a movable dichroic mirror 306. This laser light becomes a focused beam by the objective lens 305 and is able to spot-heat the microchamber 100 for cell culture. With regards to the transfer of a beam focus point, the laser beam focusing position within the microchamber 100 for cell culture can be transferred by moving the movable dichroic mirror. The laser preferably has a wavelength which is not absorbed by water and has no photochemical action. For example, at 1064 nm of an Nd:YAG laser, remarkable light absorption by water, glass or agarose does not occur, but laser beam absorption occurs selectively in the thin chromium film layer. Heat is generated only in the vicinity of the beam focus point of the thin chromium film layer in which light absorption has occurred. By this heating, as described later in full detail referring to FIG. 4, the shape of the microchamber 100 for cell culture can be changed during the cultivation.

The image data in the camera is analyzed by an image analyzer 314. In order to control, based on the various analysis results, the position of the movable dichroic mirror 306 or a movable XY stage 304 equipped with a temperature controlling function on which the microchamber 100 for cell culture has been placed, a stage moving motor 315 capable of moving the stage freely in the X-Y direction can be driven. This makes it possible to recognize the shape of the cell, keep the cell in the center of the image by pursuing the cell after recognition, or adjust the distance from the objective lens to focus to a specific cell. It is also possible to control, at a constant cycle, the movable dichroic mirror 306 or the stage 304 equipped with a temperature controlling function on which the microchamber 100 for cell culture has been placed, or to drive the stage moving motor 315 at regular intervals.

The culture solution feeding or discharging section will next be described. Plural kinds of culture solutions or culture solutions different in concentrations are fed to the microchamber 100 for cell culture from a culture solution tank 316 by using a feeder 317 which has a feeding function. The culture solution is fed to the microchamber 100 for cell culture while its temperature is adjusted by a temperature controlling mechanism in the feeder, its components of dissolved air are adjusted by a dissolved air exchange mechanism, and its flow rate is also adjusted. The culture solution, on the other hand, can be suctioned from the container 100 through a pump 318 and then sent to a waste reservoir 319.

Figure 4:
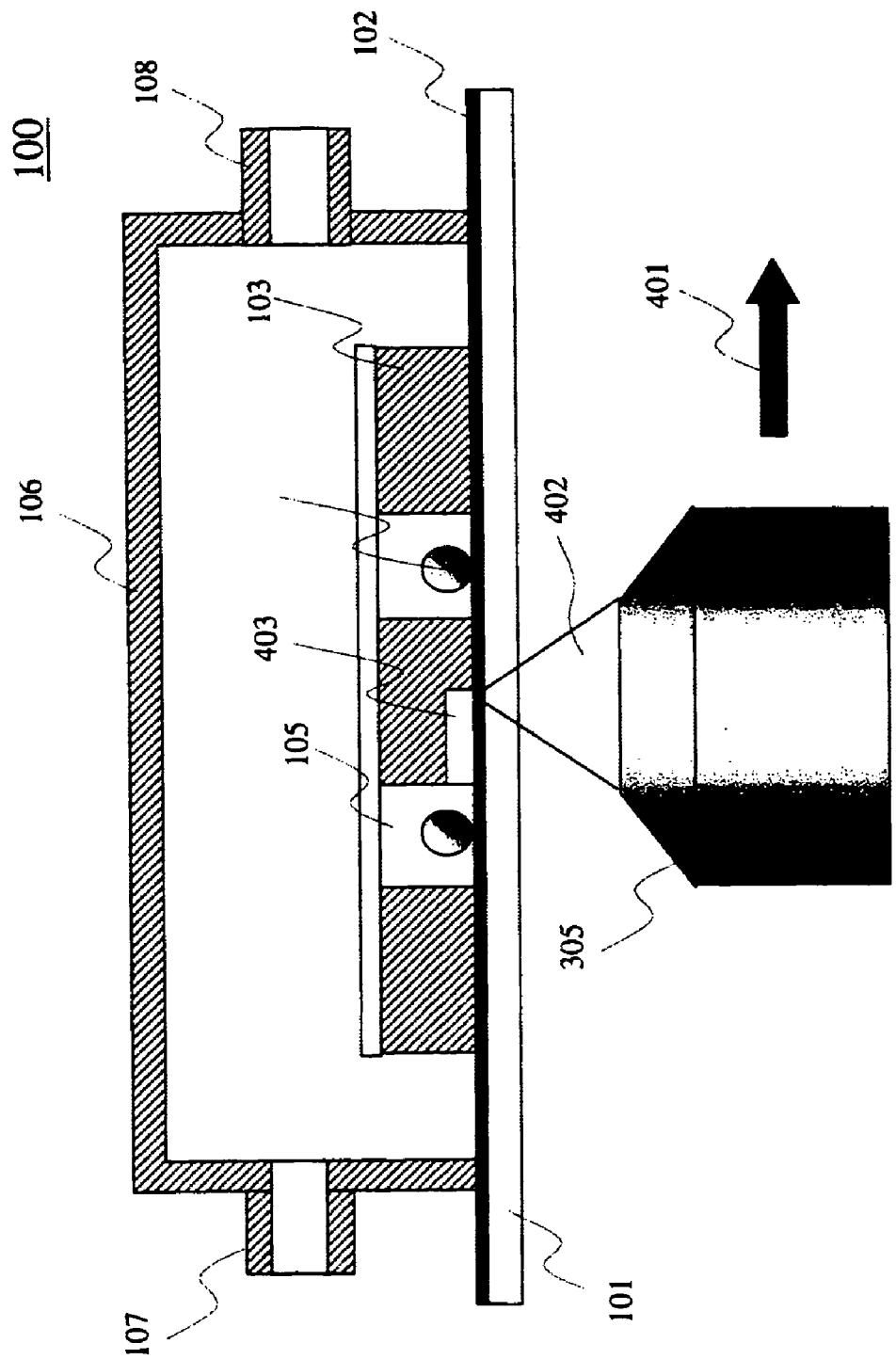
FIG. 4 is a schematic view for explaining the processing of the microchamber for cell culture by spot heating using a focused beam.

The shape change procedure of the region 103 by a focused laser beam will next be explained based on FIG. 4. A focused laser beam 402 irradiated to the microchamber 100 for cell culture by the objective lens 305 is selectively absorbed by the light absorption layer 102 and it locally generates heat in the vicinity of the irradiating position. Heat emission due to direct absorption does not occur in the other regions 101 and 103, because these regions do not absorb a focused laser beam. Owing to the heat emission of the heat absorption layer 102 at the beam focus point, the region 103 in the vicinity thereof is locally molten and molten components are diffused in an aqueous solution of the culture solution. When the position of the focused beam is transferred in the direction of an arrow 401, the region 103 in the vicinity of the light absorption layer 102 is selectively molten, leading to the formation of a tunnel 403. The diameter of the tunnel can be changed, depending on the diameter or strength of a laser to be irradiated, or a transfer rate.

Figure 5:
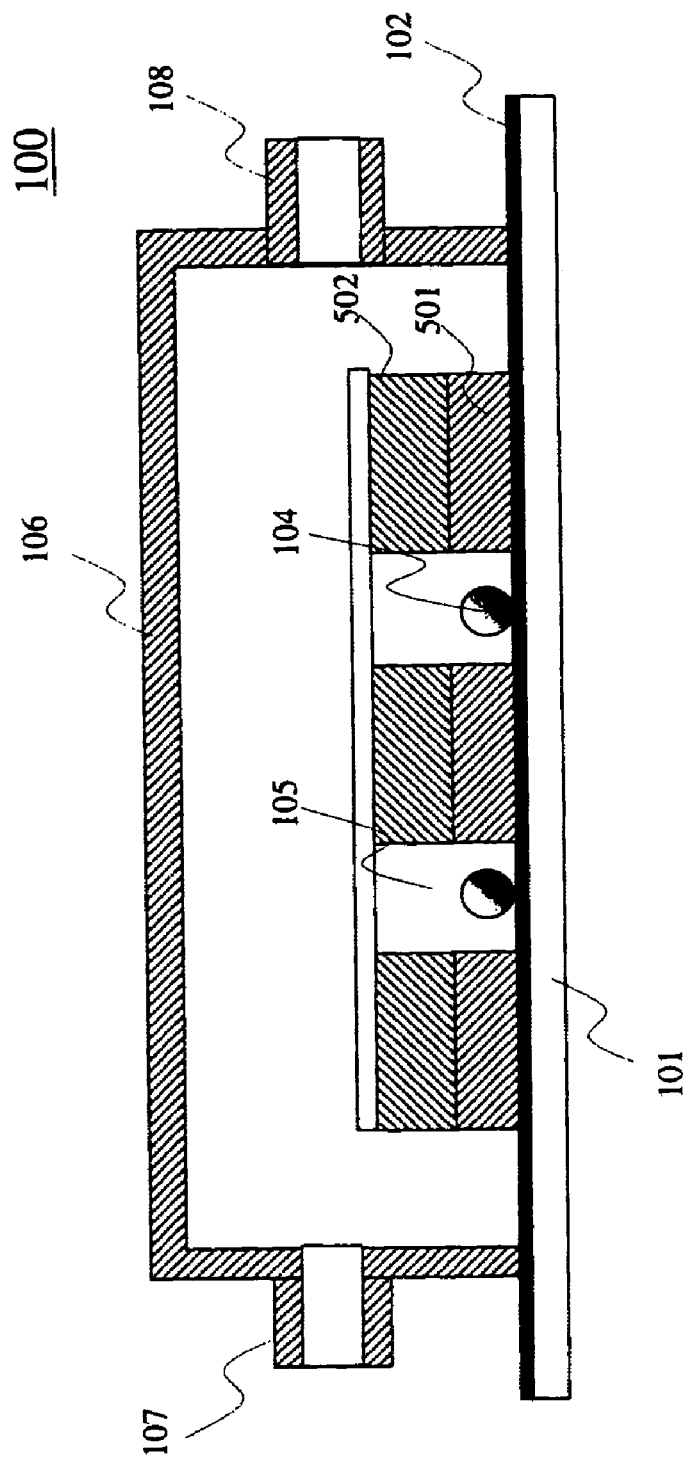
FIG. 5 is a schematic view illustrating another example of the constitution of the microchamber for cell culture.

FIG. 5 illustrates another example of the fundamental constitution of the microchamber for cell culture. In this example, the number of the region 103 which is one in the example of FIG. 1 is increased to two, that is, regions 501 and 502 which are different from each other in melting point. When the melting point of the region 501 is lower than that of the region 502, only the region 501 can be removed selectively by properly adjusting the strength of the focused beam necessary for heating. Both the regions 501 and 502 can be melted by heightening the strength of the focused beam. In this example, two regions different in melting point are stacked one after another to form two layers. Three or more layers may be formed by stacking materials different in melting point one after another. Regions different in melting point may be arranged after properly dividing them three-dimensionally. It is possible to select melting regions stepwise by adjusting the strength of the focused beam for heating. More specifically, such a constitution can be realized by stacking low-melting-point agaroses different in melting point or using materials different from each other such as agarose and plastic.

Figure 6:
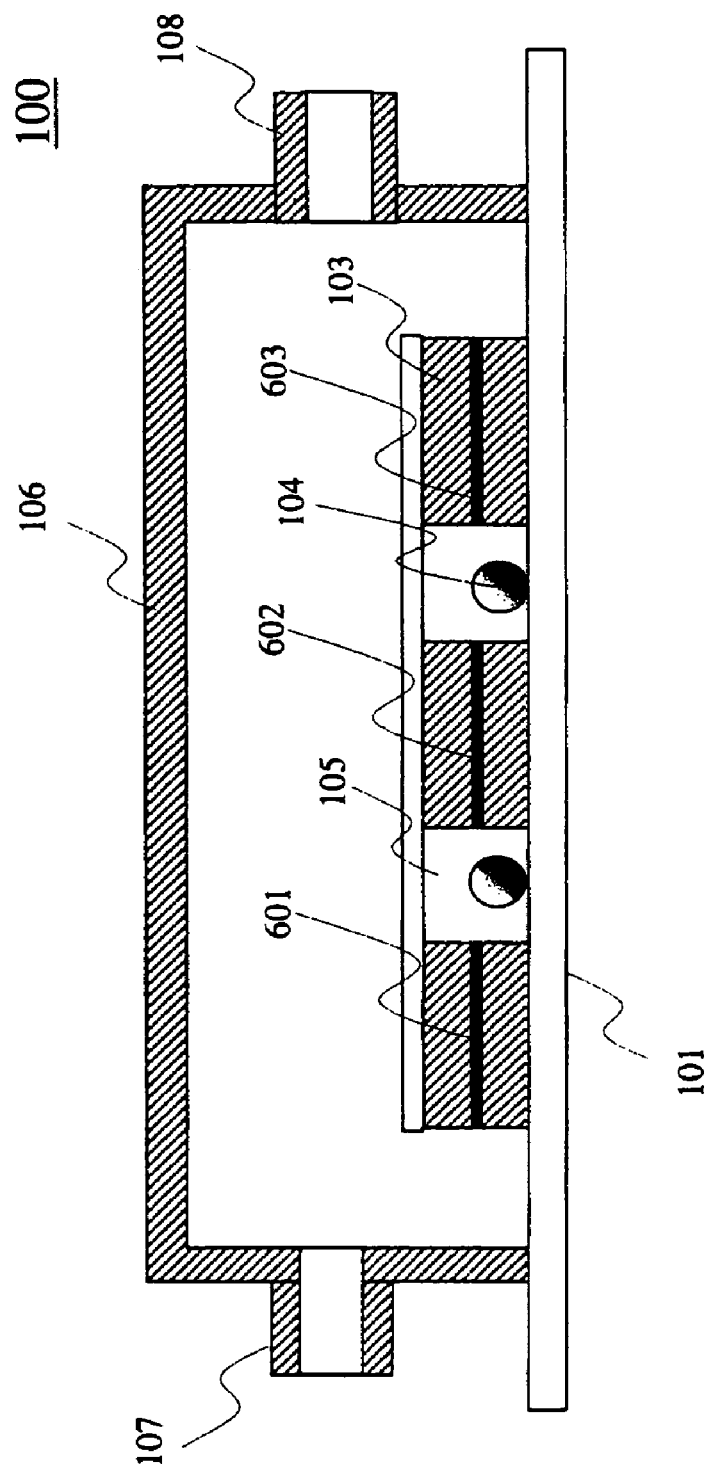
FIG. 6 is a schematic view illustrating a further example of the constitution of the microchamber for cell culture.

FIG. 6 illustrates a further example of the fundamental constitution of the microchamber for cell culture. In this example, heat absorption layers 601, 602 and 603 are placed as a fault having a specific height in the region 103. This example is characterized in that when the light absorption layers 601, 602 and 603 emit heat by heating using a focused beam, the region 103 supporting these layers are molten and the light absorption layers are therefore removed simultaneously with melting. The height of the tunnel formed by light absorption and heat generation varies depending on the position of the light absorption layer in the region 103.

Figure 7:
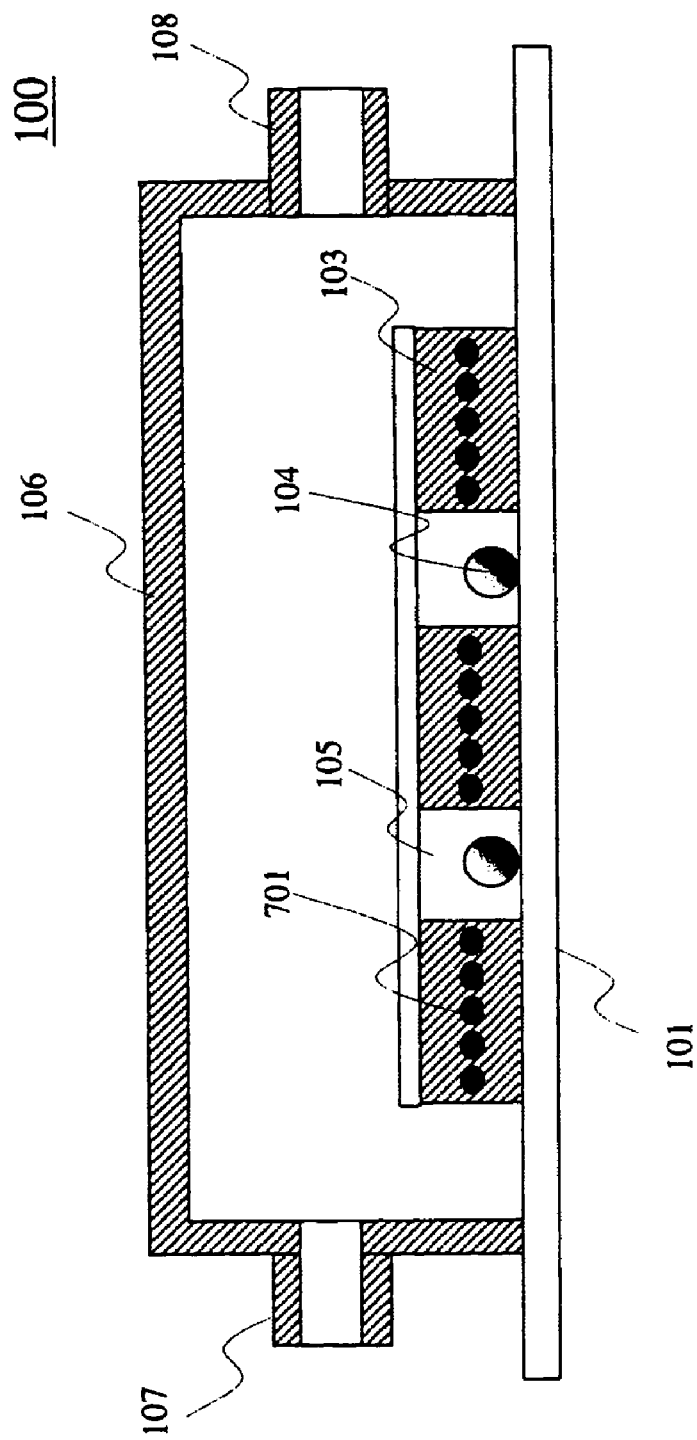
FIG. 7 is a schematic view illustrating a still further example of the constitution of the microchamber for cell culture.

The example shown in FIG. 7 is similar to that in FIG. 6 in which the light absorption layers are formed in the region 103. In this example, however, not a light absorption layer but light-absorptive fine particles 701 are used. This makes it possible to melt the whole of the region 103 exposed to a focused laser beam by arranging the fine particles 701 in the layer form and melt the region 103 in the layer form at a specific height, or dispersing the fine particle 701 uniformly in the whole of the region 103.

Figure 8:
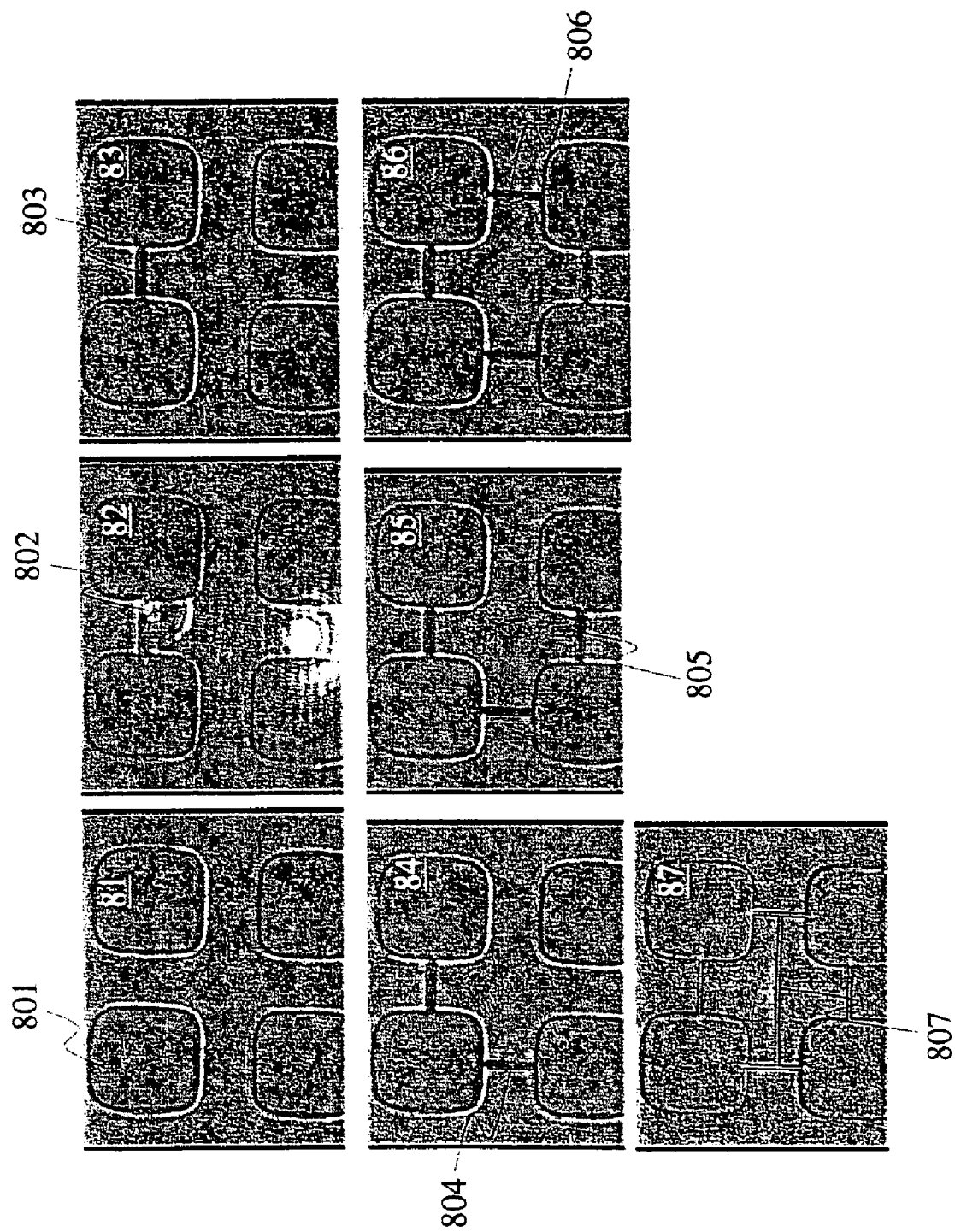
FIG. 8 is a microphotograph for explaining one example of the processing of the microchamber for cell culture by spot heating using a focused beam.

FIG. 8 illustrates one example of the actual results of melting of the region 103 using a focused beam. Over a substrate obtained by depositing chromium of 50 nm thick on a slide glass and then applying collagen to the resulting slide glass, agarose of 50 µm thick is laid. A microchamber 81 for cell culture having cavities 801 formed therein by applying a mold of 50 µm×50 µm to agarose prior to its coagulation is exposed to the focused beam of an Nd:YAG laser 802. By moving the beam while irradiating it to the microchamber, a cavity is formed as shown in the illustration of the substrate 82. After exposure, a tunnel 803 having a diameter of 5 µm is formed as shown in the illustration of the substrate 83. By carrying out similar treatments, a tunnel 804, a tunnel 805 and a tunnel 806 can be made successively as shown in the illustrations of the substrate 84, the substrate 85, and the substrate 86 successively. Moreover, a tunnel 807 connecting the tunnels thus formed can be made as shown in the illustration of the substrate 87.

Figure 9:
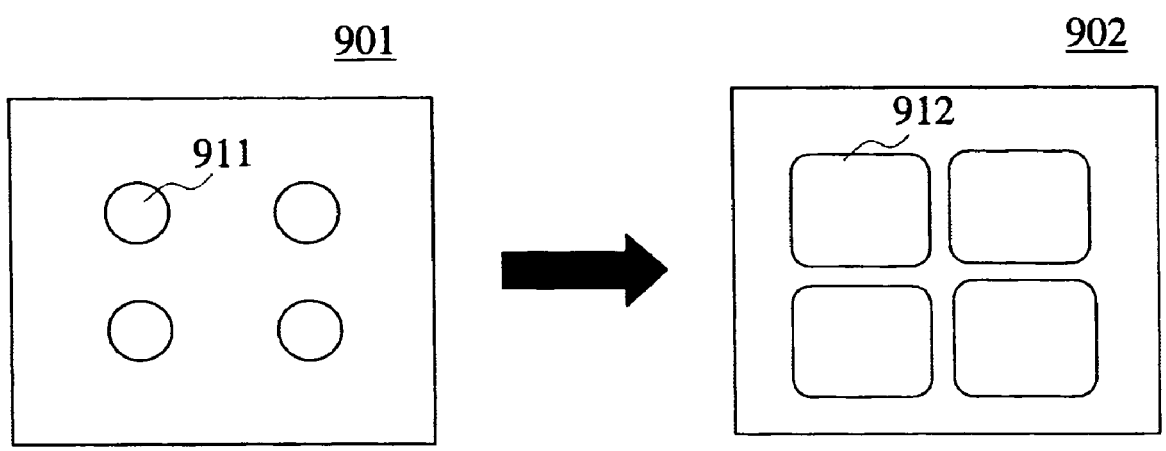
FIG. 9 is a schematic view illustrating a still further example of the constitution of the microchamber for cell culture.
Figure 10:
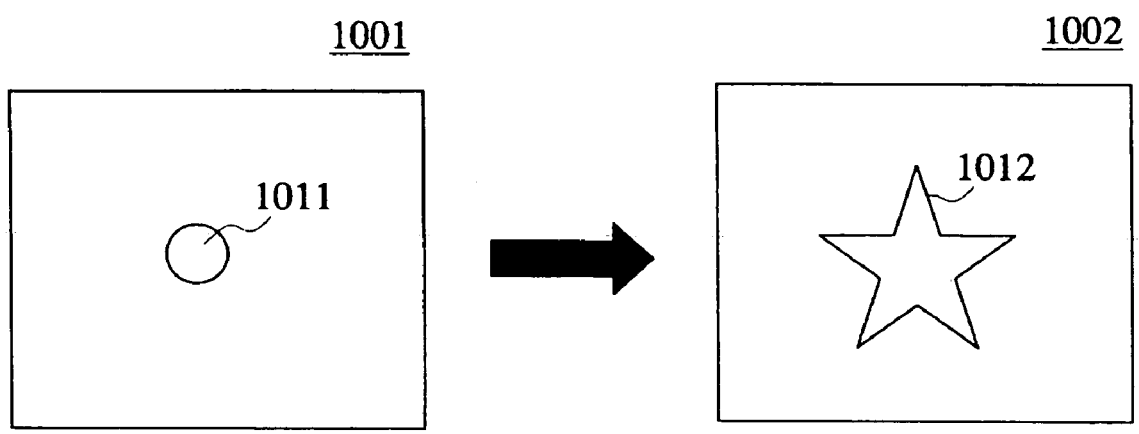
FIG. 10 is a schematic view illustrating a still further example of the constitution of the microchamber for cell culture.
Figure 1:
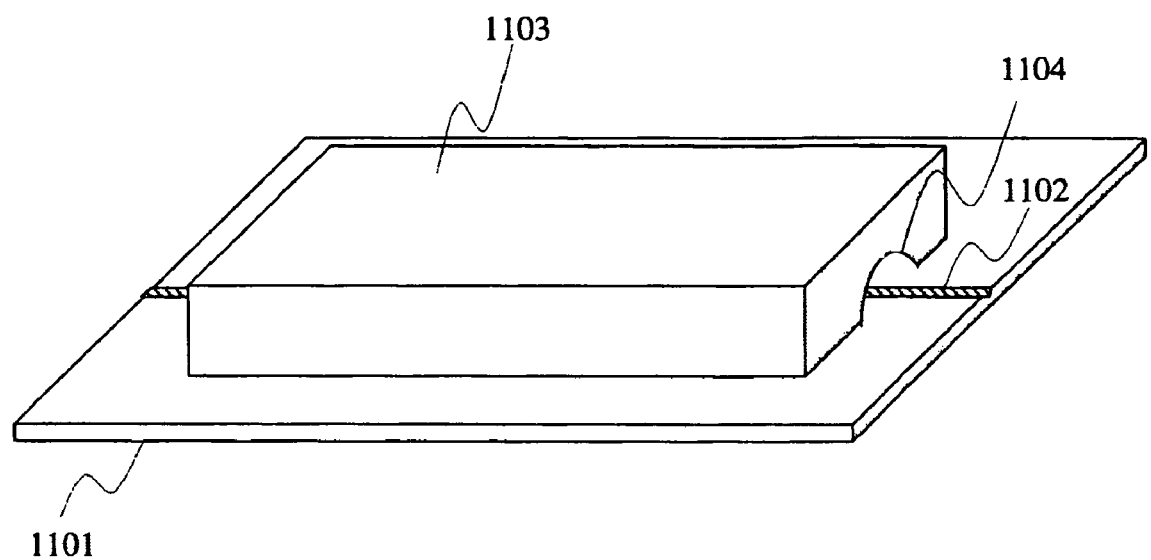

FIGS. 9 and 10 illustrate examples showing the possibility of not only forming a tunnel in the microchamber 100 for cell culture but also changing the shape of the cavities of the microchamber for cell culture. FIG. 9 shows the possibility of changing a circular cavity 911 into a square cavity 912. FIG. 10 shows the possibility of changing a circular cavity 1011 to a star-shaped cavity 1012.

FIG. 11 illustrates an example which permits spot heat generation and melting in a region smaller than the wavelength of light by using the microfabrication technology to form a light absorption region smaller than the wavelength of a focused beam. When the line width of the pattern 1102 of the light absorption layer formed by the microfabrication technology is on the submicrometer scale, exposure to a focused laser beam having a wavelength of 1064 nm selectively causes light absorption only in the pattern of the light absorption region, whereby only a region smaller than the wavelength of light can be heated locally and a tunnel 1104 is formed. This method is effective for the formation of a tunnel on the submicron scale, because a heat source can be focused only to the wavelength of light when heating is conducted using an ordinary focused beam. A similar effect can be attained by the use of light absorption submicron particles.

It is needless to say that the invention of the present application is not limited by the above-described illustration and description and a variety of modes can be employed for each of its details.

INDUSTRIAL APPLICABILITY

As described in full detail, the invention of the present application makes it possible to carry out cultivation of biological cells while changing the shape of the container depending on the cultivation stage, which has hitherto been impossible. In addition, it makes it possible to form the intended structure by melting a substance locally, that is, in a region not greater than the wavelength of light.

The invention claimed is:

1. A microchamber for cell cultures, the microchamber comprising:
    a substrate which does not absorb light of a specific wavelength;
    an absorption layer which absorbs light of the specific wavelength, said absorption layer being disposed over said substrate; and
    a region made of a solid substance which does not absorb light of the specific wavelength and has a melting point lower than the boiling point of water, said region being disposed over said substrate,
    wherein said absorption layer is disposed in said solid substance, and wherein cavities are formed in said region for cultivation of cells.

2. The microchamber of claim 1, wherein said absorption layer is composed of fine particles which absorb light of the specific wavelength, said fine particles being disposed in said solid substance.

3. The microchamber of claim 1, wherein said absorption layer is composed of a thin film disposed over said substrate.

4. The microchamber of claim 3, wherein said thin film has a thickness permitting a transmittance of visible light of 50% or greater.

5. The microchamber of claim 1, wherein said absorption layer is a thin film pattern disposed over said substrate with a line width narrower than the specific wavelength.

6. The microchamber of claim 1, wherein said solid substance has a melting point not greater than 45° C.

7. The microchamber of claim 1, wherein said solid substance is agarose.

8. The microchamber of claim 1, wherein the specific wavelength is a wavelength not absorbed by water.

9. A cell culture apparatus equipped with the microchamber for cell cultures as claimed in claim 1, the apparatus comprising:
    a unit for irradiating light of the specific wavelength to form a space by heating and melting said region made of said solid substance.

10. The cell culture apparatus according to claim 9, wherein said unit for irradiating light irradiates a focused beam.

11. The microchamber of claim 1, wherein said absorption layer is disposed in said solid substance such that a portion of said solid substance separates said absorption layer from said substrate so as to allow for a selected portion of said region to be melted.

12. A microchamber for cell cultures, the microchamber comprising:
    a substrate which does not absorb light of a specific wavelength;
    an absorption layer which absorbs light of the specific wavelength, said absorption layer being disposed over said substrate;
    a first region made of a first solid substance which does not absorb light of the specific wavelength and has a melting point lower than the boiling point of water, said first region being disposed over said substrate; and
    a second region made of a second solid substance which does not absorb light of the specific wavelength and has a melting point lower than the boiling point of water, said second region being disclosed over said substrate,
    wherein the melting point of said first region is different than the melting point of said second region, and wherein cavities are formed in said first region and said second region for cultivation of cells, each of said cavities extending through both said first region and said second region.

13. The microchamber of claim 12, wherein said absorption layer is composed of a thin film laid over a surface of said substrate, and
    wherein said first region is formed over said absorption layer.

14. The microchamber of claim 13, wherein said thin film has a thickness permitting a transmittance of visible light of 50% or greater.

15. The microchamber of claim 12, wherein said absorption layer is a thin film pattern laid over a surface of said substrate with a line width narrower than the specific wavelength.

16. The microchamber of claim 12, wherein at least one of said first solid substance and said second solid substance has a melting point not greater than 45° C.

17. The microchamber of claim 12, wherein at least one of said first solid substance and said second solid substance is agarose.

18. The microchamber of claim 12, wherein the specific wavelength is a wavelength not absorbed by water.

19. A cell culture apparatus equipped with the microchamber for cell cultures as claimed in claim 12, the apparatus comprising:

a unit for irradiating light of the specific wavelength to form a space by heating and melting at least one of said first region made of said first solid substance and said second region made of said second solid substance.

20. The cell culture apparatus according to claim 19, wherein said unit for irradiating light irradiates a focused beam.

21. The microchamber of claim 12, wherein the melting point of said first region is lower than the melting point of said second region such that said first region can be selectively melted without melting said second region.

22. The microchamber of claim 12, wherein said first region is distinct from said second region and is disposed over said second region.

* * * * *